United States Patent
Reddy

(10) Patent No.: US 7,339,052 B2
(45) Date of Patent: Mar. 4, 2008

(54) PHOSPHORAMIDITE ACTIVATOR FOR OLIGONUCLEOTIDE SYNTHESIS

(75) Inventor: Kalakota S. Reddy, Midland, MI (US)

(73) Assignee: Honeywell International Inc., Morristown, NJ (US)

(*) Notice: Subject to any disclaimer, the term of this patent is extended or adjusted under 35 U.S.C. 154(b) by 531 days.

(21) Appl. No.: 11/053,733

(22) Filed: Feb. 8, 2005

(65) Prior Publication Data

US 2006/0178509 A1    Aug. 10, 2006

(51) Int. Cl.
   C07H 21/00    (2006.01)
   C07D 257/00   (2006.01)
   C07D 233/54   (2006.01)
(52) U.S. Cl. ............... 536/25.34; 548/251; 548/355.1
(58) Field of Classification Search .................. None
   See application file for complete search history.

(56) References Cited

U.S. PATENT DOCUMENTS

| | | | |
|---|---|---|---|
| 3,687,808 A | 8/1972 | Merrigan et al. | 536/27 |
| 5,212,295 A | 5/1993 | Cook | 536/26.7 |
| 5,824,793 A | 10/1998 | Hirschbein et al. | 536/25.34 |
| 6,166,197 A | 12/2000 | Cook et al. | 536/24.5 |
| 6,274,725 B1 | 8/2001 | Sanghvi et al. | 536/25.34 |
| 6,642,373 B2 | 11/2003 | Monoharan et al. | 536/25.34 |
| 7,148,219 B2* | 12/2006 | Lou et al. | 514/235.5 |
| 2003/0069410 A1 | 4/2003 | Ravikumar | |
| 2006/0004069 A1* | 1/2006 | Momose et al. | 514/383 |

OTHER PUBLICATIONS

Noe and Kaufhold, "9 Chemistry of Antisense Oligonucleotides," New Trends in Synthetic Medicinal Chemistry,Wiley-VCh, Weinheim, 2000, 261-347.
Applied BioSystems User's Manual for Models 392 and 394 DNA/RNA Synthesizers; Section 6 Chemistry for Automated DNA/RNA Synthesis (Mar. 1994).
http://www.eurogentec.be/ code/EN/what.asp?pk_id_what=85)—Feb. 8, 2005.
Claudia Hobartner et al. "The Synthesis of 2'-0-[Triisopropylsilyl)oxy] methly (TOM) Phosphoramidites of Methylated Ribonucleosides for Use in Automated RNA Solid-Phase Synthesis," Monatshefte Fur Chemie 134, 851-873 (2003).
Chandra Vargeese, et al. "Efficient activiation of nucleoside phosphoramidites with 4,5-dicyanoimidazole during oligonucleotide synthesis," 1046-1050 Nucleic Acids Research, 1998, vol. 26, No. 4.
www.glenres.com/GlenReports/GR10-1.pdf—Feb. 8, 2005.
Wagner et al., Nucleosides & Nucleotides, 1997, 17, pp. 1657-1660.
Bhan et al., Nucleosides & Nucleotides, 1997, 17, pp. 1195-1199.
X. Wu and S. Pitsch, *Nucleic Acids Research* 1998, vol. 26, No. 19, pp. 4315-4323).
Ouchi, et al., *Drug Design and Discovery* 1992, vol. 9, pp. 93-105.
Ravasio, et al., *J. Org. Chem.* 1991, 56, pp. 4329-4333.
Secrist, et al., "Abstract 21, Program & Abstracts", Tenth International Roundtable, *Nucleosides, Nucleotides and their Biological Applications*, Park City, Utah, Sep. 16-20, 1992.
Greene and Wuts, *Protective Groups in Organic Synthesis*, Chapter 7, 2d ed, John Wiley & Sons, New York, 1991.
Englisch et al., *Angewandte Chemie*, International Edition 1991, vol. 30, No. 6, pp. 613-629.
Limbach, A., et al., *Nucleic Acids Research*, 1994, vol. 22, No. 12, 2183-2196.
Alul, et al., Nucleic Acids Research 1991, vol. 19, No. 7, 1527-1532.
TentaGel Support, An Aminopolyethyleneglycol Derivatized Support (see, e.g., Wright, et al., Tetrahedron Letters 1993, vol. 34, No. 21, pp. 3373-3376.
M.J. Gait, "Oligonucleotide Synthesis, A Practical Approach", IRL Press at Oxford University Press (1984, ISBN 0-904147-74-6).
S. Pitsch, et al. Helvetica Chimica Acta—vol. 84 (2001) pp. 3773-3795.
V. Serebryany and L. Beigelman, "An efficient preparation of protected ribonucleosides for phosphoramidite RNA Synthesis," Tetrahedron Letters 43 (2002) pp. 1983-1985.
Welz R, et al "5-(Benzylmercapto)-1H-Tetrazole as Activator for 2'-0-TBDMS Phosphoramidite Building Blocks in RNA Synthesis" vol. 43, No. 5 pp. 795-797 dated Jan. 28, 2002 XP004332810.
Stutz Alfred, et al "Novel Fluoride-Labile Nucleobase-Protecting Groups for the Synthesis of 3'(2')-0-Amino-Acylated RNA Sequences" vol. 83, No. 9 pp. 2477-2503 dated 2000 XP002979645.

* cited by examiner

*Primary Examiner*—L. E. Crane
(74) *Attorney, Agent, or Firm*—Erika S. Wilson

(57) ABSTRACT

The present invention provides an improved phosphoramidite activator comprising a solution of 5-benzylmercaptotetrazole in acetonitrile and N-alkyimidazole. Further provided are improved methods of oligonucleotide synthesis wherein a phosphoramidite activator comprising a solution of 5-benzylmercaptotetrazole in acetonitrile and N-alkyimidazole is used to prepare internucleoside linkages.

16 Claims, No Drawings

SEQUENCE LISTING

<160> NUMBER OF SEQ ID NOS: 4

<210> SEQ ID NO 1
<211> LENGTH: 21
<212> TYPE: RNA
<213> ORGANISM: Artificial
<220> FEATURE:
<223> OTHER INFORMATION: RNA 21-mer

<400> SEQUENCE: 1
gcccauaucg uuucauagcu u                                         21

<210> SEQ ID NO 2
<211> LENGTH: 20
<212> TYPE: RNA
<213> ORGANISM: Artificial
<220> FEATURE:
<223> OTHER INFORMATION: RNA 20-mer

<400> SEQUENCE: 2
uuuuuuuuuu uuuuuuuuuu                                           20

<210> SEQ ID NO 3
<211> LENGTH: 20
<212> TYPE: DNA
<213> ORGANISM: Artificial
<220> FEATURE:
<223> OTHER INFORMATION: DNA 20-mer

<400> SEQUENCE: 3
gcccaagctg gcatccgtca                                           20

<210> SEQ ID NO 4
<211> LENGTH: 20
<212> TYPE: DNA
<213> ORGANISM: Artificial

```
<220> FEATURE:
<223> OTHER INFORMATION: DNA 20-mer

<400> SEQUENCE: 4
ggctaaatcg ctccaccaag                                                 20
```

PHOSPHORAMIDITE ACTIVATOR FOR OLIGONUCLEOTIDE SYNTHESIS

FIELD OF INVENTION

The present invention relates to an improved composition for oligonucleotide synthesis. More specifically, the present invention relates to an improved phosphoramidite activator and related methods of using the same for oligonucleotide synthesis.

BACKGROUND

Oligonucleotide synthesis has been found to be extremely useful in making primers for polymerase chain reaction (PCR) replication. In particular, oligonucleotides can be tailored to bind to a particular region of complementary DNA thereby allowing specific segments of DNA to be amplified. This aspect of oligonucleotides has created an interest in using oligonucleotides in therapeutic and diagnostic applications, and specifically for use in modifying gene and protein function in a sequence specific manner. For these and other applications, oligonucleotides must be produced in large quantities and be of high purity.

DNA and RNA oligonucleotide synthesis involves the bonding of multiple nucleosides in series. This process generally requires the steps of (1) the de-blocking of the 5'-hydroxyl group on a first nucleoside, nucleotide, or oligonucleotide; (2) activation of a phosphoramidite monomer base; (3) binding the first activated nucleoside to the activated phosphoramidite via phosphite linkage; and (4) oxidizing the phosphite linkage to form a more stable phosphate linkage. These four steps can be repeated until the desired oligonucleotide is produced.

Phosphoramidites are, therefore, important as building blocks in the synthesis of oligonucleotides. Phosphoramidites for a variety of nucleosides are commercially available through a variety of vendors. 3'-O-phosphoramidites are the most widely used amidites, but the synthesis of oligonucleotides can also involve 5'-O- and 2'-O-protected phosphoramidites (Wagner et al., Nucleosides & Nucleotides, 1997, 17, 1657-1660; Bhan et al., Nucleosides & Nucleotides, 1997, 17, 1195-1199). There are also many phosphoramidites available that are not nucleosides (Cruachem Inc., Dulles, Va.; Clontech, Palo Alto, Calif.).

As indicated above, oligonucleotide synthesis typically involves the coupling of a 3'-O-phosphoramidite to a 5'-OH group of a nucleoside, nucleotide, or oligonucleotide. One of the steps in this synthesis process is the activation of the phosphoramidite which is achieved by cleaving off one of the groups protecting the phosphorous linkage. The resulting activated phosphorous is then able to bond to the active 5'-hydroxyl group of the nucleoside base. An example of this reaction is shown in the scheme below wherein a phosphoramidite (I) is reacted with an oligonucleoside (II) bound to the primer support in the presence of a phosphoramidite activator to form an internucleoside linkage (III):

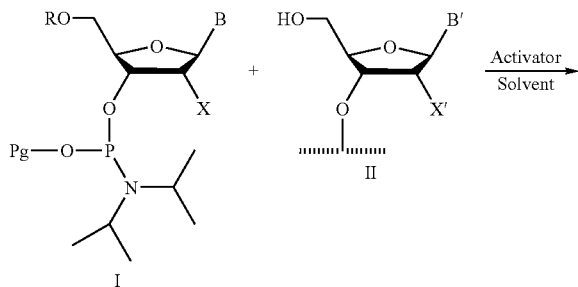

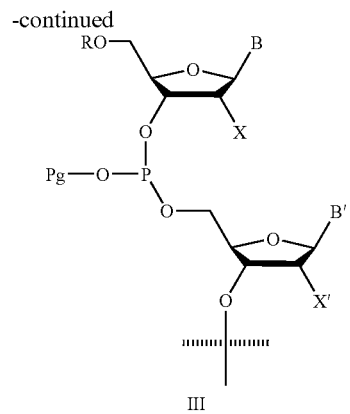

III

In this example, R is moiety such as dimethoxytrityl (DMT), 2'-O-(tert-butyl)-dimethylsilyl (TBDMS), 2'-O-[(triisopropyl-silyl)oxy]methyl (TOM), oligonucleotides and analogs thereof, or the like; Pg is a phosphorous protecting group such as alkyl, —CH$_2$CH$_2$CN, —CH$_2$CH═CHCH$_2$CN, para-CH$_2$C$_6$H$_4$CH$_2$CN, —(CH$_2$)$_{2-5}$N(H)COCF$_3$, —CH$_2$CH$_2$Si(C$_6$H$_5$)$_2$CH$_3$, CH$_2$CH$_2$N(CH$_3$)COCF$_3$, and the like; X and X' are independently hydrogen, fluoro, alkoxy, —O-tert-butyldimethyl silyl (OTBDMS), —O-methoxy methyl (OMOM), 2'-O-methoxyethyl (2'-O-MOE), or the like; and B and B' are independently a moiety derived from adenine, cytosine, guanine, thymine, or uracil.

Oligonucleotides formed via the above-mentioned scheme are known in the art, see e.g. Rüdiger Welz and Sabine Müller, "5-Benzylmercapto-1H-tetrazole as activator for 2'O-TBDMS phosphoramidite building blocks in RNA synthesis", Tetrahedron Letters 43, 2002, p. 795-97. To supply the growing demand for these oligonucleotides, there is a desire to improve the synthesis of oligonucleotides on a commercial scale (Noe, Kaufhold, New Trends in Synthetic Medicinal Chemistry, Wiley-VCh Weinheim, 2000, 261). To this end, much effort has been expended in developing phosphoramidite activators.

The first activator described for phosphoramidite chemistry was 1H-tetrazole. Subsequently, more potent activators have been developed including 5-methylthio-1H-tetrazole, 5-nitrophenyl-1H-tetrazole, 5-ethylthio-1H-tetrazole, and 4,5-dicyanoimidazole. More recently, 5-benzylmercaptotetrazole (BMT) (also known as benzylthiotetrazole (BTT)) was introduced as an ideal activator for certain RNA synthesis techniques such as activation of TOM-protected and TBDMS-protected RNA phosphoramidites. See e.g. X. Wu and S. Pitsch, Nucleic Acitds Research, 1998, 26, 4315-23); S. Pitsch, et al., Helv. Chim. Acta, 2001, 84, 3773-3795; and R. Welz and S. Müller, "5-Benzylmercapto-1H-tetrazole as activator for 2'O-TBDMS phosphoramidite building blocks in RNA synthesis", Tetrahedron Letters 43, 2002, p. 795-97.

BMT allows for efficient RNA synthesis with as much as 50% less TBDMS or TOM monomer as compared to that required by processes using 1H-tetrazole. In addition, BMT has a higher solubility at lower temperatures than does 1H-tetrazole and BMT does not crystallize or clog lines below 19° C. However, it has been reported that BMT's maximum solubility in acetonitrile is about 0.33M (see http://www.eurogentec.be/code/EN/what.asp?pk_id_what=85) and the hydrophobic nature of BMT has limited its commercial use in acetonitrile to solutions less than or equal to 0.25M. Above that concentration, the BMT in acetonitrile becomes unstable and tends to clog reagent lines in commercial operations. As a result, commercial use of BMT in acetonitrile have been limited to concentrations less than or equal to 0.25M although solutions above 0.3M could advantageously lead to more efficient and rapid activation and less phosphoramidite waste. In addition, BMT in acetonitrile above 0.3M is safer and not explosive and, therefore, can be made in large quantities and stored and shipped in metal containers, such as 200L stainless steel pressure dispensing systems.

Applicant have overcome these and other shortcomings of the prior art with the present invention.

DESCRIPTION OF INVENTION & PREFERRED EMBODIMENTS

The present invention describes an improved phosphoramidite activator solution for oligonucleotide synthesis. Specifically, Applicants have discovered that the concentration of 5-benzylmercaptotetrazole (BMT) (also known as benzylthiotetrazole (BTT) or) in acetonitrile can be increased via the addition of certain polar co-solvents such as an N-alkylimidazole, tetrahydrofan, and dioxane. Co-solvents that may be utilized in the present invention must be capable of dissolving phosphoramidites and their functionality must not hinder conventional DNA and RNA synthesis techniques. A preferred co-solvent is an N-alkylimidazole. Solutions of BMT in acetonitrile and an N-alkylimidazole have been found to be stable at concentrations above 0.25M. When used as a phosphoramidite activator, solutions of BMT above 0.25M allow for increased phosphoramidite activation, thereby leading to more efficient and rapid oligonucleotide synthesis with less phosphoramidite waste.

Phosphoramidites according to the present invention are compounds of Formula I:

(Formula I)

wherein

Pg is a phosphorous protecting group such as alkyl, —CH$_2$CH$_2$CN, —CH$_2$CH=CHCH$_2$CN, para-CH$_2$C$_6$H$_4$CH$_2$CN, —(CH$_2$)$_{2-5}$N(H)COCF$_3$, —CH$_2$CH$_2$Si(C$_6$H$_5$)$_2$CH$_3$, —CH$_2$CH$_2$N(CH$_3$)COCF$_3$;

R$^1$ is a nucleoside or an oligonuceloside; and

R$^2$ is morpholino, dialkylamino, or —N(R$^3$)$_2$, wherein R$^3$ is independently C$_1$-C$_6$ alkyl or 4-7 member heterocycloalkyl or heterocycloalkyenyl ring having up to 3 heteroatoms selected from the group consisting of nitrogen, sulfur, and oxygen.

Nucleosidic compounds according to the present invention include monomeric and linked DNA or RNA nucleosides. The term "nucleoside" is intended to include naturally or non-naturally occurring nucleosides and nucleosides having modified nucleobases and/or modified sugar moieties, including Linked Nucleic Acid (LNA) derivatives and nucleosides substituted with additional groups, e.g. halogene substituents, Detector-containing nucleosides, including Biotin- or Fluorescein-linked compounds; Effector-containing compounds with ligands enhancing antisense action; as well as oligomeric structures derived from two or more of these. Examples of suitable DNA and RNA nucleosides include protected nucleosides, such as 5'-O-protected nucleosides (with or without additional N-protection, such as protection via benzoyl, isobutyryl, tert-butylphenoxyacetyl "TAC", and the like), including 5'-O-protected nucleosides of Adenosine, Cytidine, Guanosine, Thymidine, deoxyAdenosine, deoxyCytidine, and deoxyGuanosine; 5'-O-protected-2'-protected nucleosides, (with or without additional N-protection), including 5'-O-protected-2'-protected nucleosides of Adenosine, Cytidine, Guanosine, and Uridine (wherein preferred 2'-protecting groups include t-butyldimethylsilyl, methoxymethyl (MOM), methoxyethyl (MOE) and alkoxy, such as, methoxy, groups), as well as 3'-O-protected nucleosides of Adenosine, Cytidine, Guanosine, Thymidine, Uridine, deoxyAdenosine, deoxyCytidine, and deoxyGuanosine, (with or without additional N-protection) and oligomeric structures derived therefrom. Internucleoside linkages between linked nucleosides comprise native phosphodiester linkages as well as modified linkages such as phosphoro-thioate linkages. Other internucleoside linkages as is known in the art are also amenable to the present invention.

Sugar modifications are known in the prior art and include for example 2' substituents such as F and 2'-O-substituents such as substituted or unsubstituted C$_1$-C$_{10}$ alkyl, C$_2$-C$_{10}$ alkenyl, C$_2$-C$_{10}$ alkynyl, ethers and polyethers wherein the substitutions are selected from one or several amino, imidazole, halogen, cyano, carboxy, hydroxy, nitro and mercapto residues. Preferred polyethers are linear and cyclic polyethylene glycols (PEGs), and (PEG)-containing groups, such as crown ethers and those which are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249, each of which are hereby incorporated by reference. Further sugar modifications are disclosed in Cook, P. D., supra. Fluoro, O-alkyl, O-alkylamino, O-alkyl imidazole, O-alkylaminoalkyl, and alkyl amino substitutions are described in U.S. patent application Ser. No. 08/398,901, filed Mar. 6, 1995, now U.S. Pat. No. 6,166,197 entitled "Oligomeric Compounds having Pyrimidine Nucleotide(s) with 2' and 5' Substitutions", which is hereby incorporated by reference.

Sugars having O-substitutions on the ribosyl ring are also amenable to the present invention. Representative substitutions for ring O include S, CH$_2$, CHF, and CF$_2$, see, e.g., Secrist, et al., "Abstract 21, Program & Abstracts", Tenth International Roundtable, *Nucleosides, Nucleotides and their Biological Applications*, Park City, Utah, Sep. 16-20, 1992, hereby incorporated by reference.

As used herein, the term "alkyl" includes but is not limited to straight chain, branch chain, and alicyclic hydrocarbon groups. Alkyl-groups of the present invention may be substituted. Representative alkyl-substituents are disclosed in U.S. Pat. No. 5,212,295, at column 12, lines 41-50, hereby incorporated by reference.

"Aryl" groups are aromatic cyclic compounds including but not limited to phenyl, naphthyl, anthracyl, phenanthryl, pyrenyl, and xylyl.

In general, the term "hetero" denotes an atom other than carbon, preferably but not exclusively N, O, or S. Accordingly, the term "heterocycloalkyl" denotes an alkyl ring system having one or more heteroatoms (i.e., non-carbon atoms). Preferred heterocycloalkyl groups include, for example, morpholino groups. As used herein, the term "heterocycloalkenyl" denotes a ring system having one or more double bonds, and one or more heteroatoms. Preferred heterocycloalkenyl groups include, for example, pyrrolidino groups.

In some preferred embodiments of the invention amino groups are appended to alkyl or other groups, such as, for example, 2'-alkoxy groups (e.g., where R$^1$ is alkoxy). Such amino groups are also commonly present in naturally occurring and non-naturally occurring nucleobases. It is generally preferred that these amino groups be in protected form during the synthesis of oligomeric compounds of the invention. Representative amino protecting groups suitable for these purposes are discussed in Greene and Wuts, *Protective Groups in Organic Synthesis*, Chapter 7, 2d ed, John Wiley & Sons, New York, 1991. Generally, as used herein, the term "protected" when used in connection with a molecular moiety such as "nucleobase" indicates that the molecular moiety contains one or more functionalities protected by protecting groups.

As used in the present application the term "nucleobase" is intended to include naturally occurring nucleobases such as for example adenine, guanine, cytosine, uridine, and thymine, as well as nucleobases that are modified such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-aza uracil, cytosine and thymine, 5-uracil (pseudo uracil), 4-thio uracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the *Concise Encyclopedia Of Polymer Science And Engineering,* pages 858-859, Kroschwitz, J. I., ed. John Wiley & Sons, 1990, and those disclosed by Englisch et al., *Angewandte Chemie,* International Edition 1991, 30, 613, Limbach, A., et al., *Nucleic Acids Research,* 1994, 22, 2183-2196. The term "nucleosidic base" is further intended to include heterocyclic compounds that can serve as like nucleosidic bases including certain "universal bases" that are not nucleosidic bases in the most classical sense but serve as nucleosidic bases. Especially mentioned as a universal base is 3-nitropyrrole.

Modified internucleoside linkages are known in the prior art and include for example methylphosphonates, monothiophosphates, dithiophosphates, phosphoramidates, phosphate esters, bridged phosphoroamidates, bridged phosphorothioates, bridged methylenephosphonates, dephospho internucleotide analogs with siloxane bridges, carbonate bridges, carboxymethyl ester bridges, acetamide bridges, carbamate bridges, thioether, sulfoxy, sulfono bridges, various "plastic" DNAs, α-anomeric bridges, and borane derivatives.

The efficiency of the phosphoramidite activation directly correlates to the final product yield during oligonucleotide synthesis. This efficiency can be improved by providing a phosphoramidite activator solution having a higher concentration of BMT. Applicants have discovered that the solubility of BMT in acetonitrile can be increased via the addition of an N-alkylimidazole as a co-solvent. Accordingly, one aspect of the present invention provides a phosphoramidite activator composition comprising BMT in acetonitrile and from about 0.1% to about 10% N-alkylimidazole. In a preferred embodiment, the activator composition of the present invention comprises from about 0.1% to about 1.5% an N-alkylimidazole, more preferably from about 0.5% to about 1.5% an N-alkylimidazole, and even more preferably from about 1.0% to about 1.5% an N-alkylimidazole. Concentrations of an N-alkylimidazole above 10% may interfere with the DNA or RNA synthesis processes. Preferably, the N-alkyimidazole is N-methylimidazole.

In another. preferred embodiment, the phosphoramidite activator composition comprises a solution having from about 0.25 to about 1.0 molar concentration of BMT in synthesis grade acetonitrile. More preferred, the composition comprises from about 0.30 to about 0.40 molar solution of BMT, while even more preferred is a composition from about 0.35 to about 0.40 molar solution of BMT. Preferably, the composition is maintained at a temperature above about $-1°$ C., and more preferably above about 4° C. Prolonged exposure of the composition to temperatures below $-4°$ C. can cause precipitates to form in the solution which can negatively impact commercial oligonucleotide synthesis processes.

According to another aspect of the present invention, provided are novel methods for phosphoramidite activation. Without being bound by any particular theory, it is believed that the mechanism by which BMT activates a phosphoramidite involves first the protonation of the phosphoramidite's trivalent phosphorous and attachment of a morpholino, dialkylamino, or amine leaving group to form an intermediate product. Subsequently, leaving group is displaced allowing the phosphorous to bind to an available 5'-O site of a nucleoside or oligonucleotide, thereby creating a covalent intersugar linkage within a oligonucleotide. An example of this reaction mechanism is shown in the scheme:

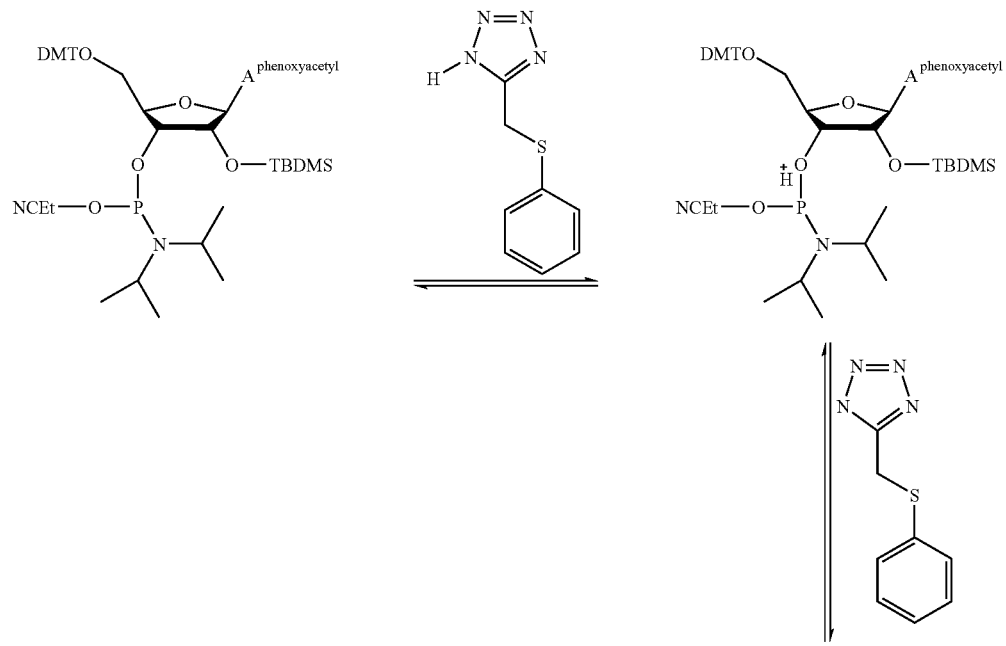

-continued

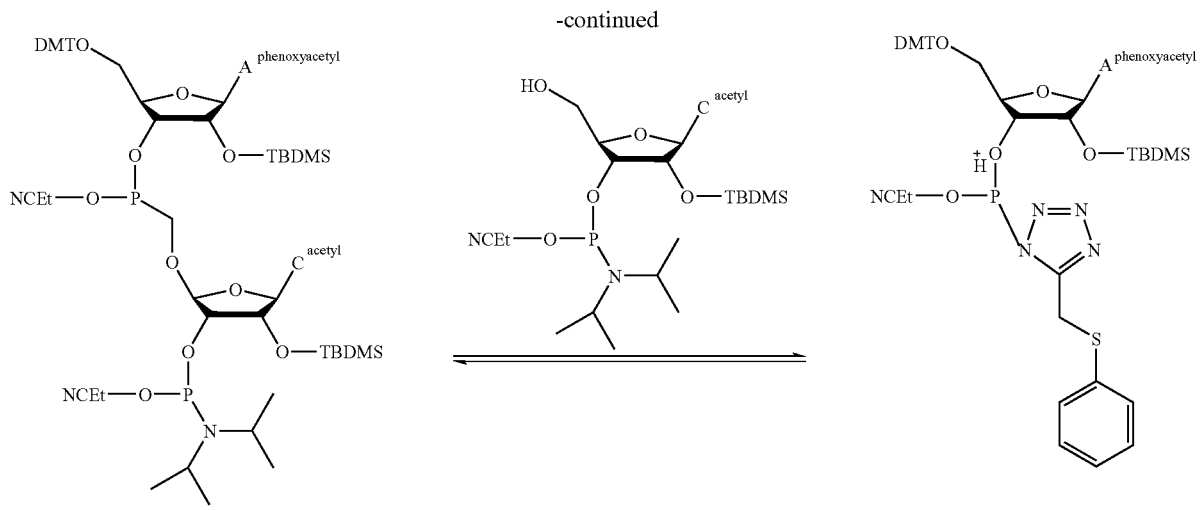

The reaction of the phosphoramidite and the hydroxyl group in the presence for the phosphoramidite activator can be preformed in the presence of a solvent, such as acetonitrile.

Thus, in some preferred embodiments, the present invention is directed to methods for preparing covalent intersugar linkages including those represented by a compound having the Formula II:

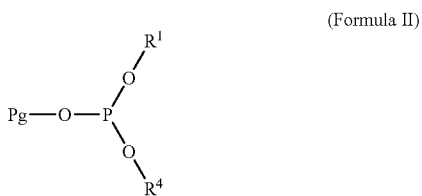

(Formula II)

wherein Pg and $R^1$ are defined as above; and
$R^4$ is a nucleoside or a oligonucleoside.

comprising the steps of
(a) providing a phosphoramidite of Formula I; and
(b) reacting said phosphoramidite with a hydroxyl group of sugar moiety of a nucleoside or an oligonucleoside in the presence of a phosphoramidite activator;
wherein said phosphoramidite activator comprises a solution of greater than 0.25M BMT in acetonitrile and an N-alkylimidazole.

In certain preferred embodiments, $R^4$ is liked to a solid support, as in for example, standard solid phase oligonucleotide synthetic regimes. Solid supports according to the invention include those generally known in the art to be suitable for use in solid phase methodologies, including, for example, controlled pore glass (CPG), oxalyl-controlled pore glass (see, e.g., Alul, et al., Nucleic Acids Research 1991, 19, 1527, hereby incorporated by reference in its entirety), TentaGel Support, an aminopolyethyleneglycol derivatized support (see, e.g., Wright, et al., Tetrahedron Letters 1993, 34, 3373, hereby incorporated by reference in its entirety) and Poros, a copolymer of polystyrene/divinylbenzene.

Also provided in accordance with the present invention are methods for the preparation of an oligonucleotide comprising the steps of:

(a) provided a 3'-mononucleoside phosphoramidite or a 3'-oligonucleoside phosphoramidite; and
(b) reacting said 3'-mononucleoside phosphoramidite or 3'-oligonucleoside phosphoramidite with the 5'hydroxyl of a nucleoside, nucleotide, or oligonucleotide in the presence of a phosphoramidite activator;
said phosphoramidite activator comprising a solution of greater than 0.25M BMT in acetonitrile and an N-alkylimidazole.

As used herein, the term "oligonucleotide" is intended to include both naturally occurring and non-naturally occurring (i.e., "synthetic") oligonucleotides. Naturally occurring oligonucleotides are those which occur in nature; for example ribose and deoxyribose phosphodiester oligonucleotides having adenine, guanine, cytosine, thymine and uracil nucleobases. As used herein, non-naturally occurring oligonucleotides are oligonucleotides that contain modified sugar, internucleoside linkage and/or nucleobase moieties. Such oligonucleotide analogs are typically structurally distinguishable from, yet functionally interchangeable with, naturally occurring or synthetic wild type oligonucleotides. Thus, non-naturally occurring oligonucleotides include all such structures which function effectively to mimic the structure and/or function of a desired RNA or DNA strand, for example, by hybridizing to a target.

In some preferred embodiments, the 3'-mononucleoside phosphoramidite or 3'-oligonucleoside phosphoramidite is reacted with the 5'hydroxyl of a solid-support bound nucleoside, nucleotide, or oligonucleotide.

In further preferred embodiments, each of the foregoing methods, are preformed iteratively to produce an oligonucleotide or analog thereof having a preselected nucleotide base sequence.

In general, the phosphous protecting groups, designated "Pg" are removed at the end of the synthetic regime, preferably at the time that the completed oligonucleotide or analog is cleaved from the solid support.

As will be recognized by those of skill in the art, oligonucleotides may be synthesized according to the present methods, not only via the batch and/or continuous processes, but also using automated oligonucleotide synthesis techniques, as described, for example, in Applied BioSystems User's Manual for Models 392 and 394 DNA/RNA Synthesizers; Section 6 Chemistry for Automated DNA/RNA Synthesis (March 1994) and M. J. Gait, "Oligonucleotide Synthesis, A Practical Approach", IRL Press at Oxford University Press (1984, ISBN 0-904147-74-6), which are incorporated herein by reference. In such embodiments, a nucleoside and/or oligonucleotide hydroxyl-containing compound is immobilized on a solid support and reacted within an automated DNA Synthesizer with a nucleoside phosphitylating agent in the presence of a phosphitylation activator to form an oligonucleotide. A specified number and sequence of phosphitylation reactions may be conducted to produce oligonucleotides comprising different lengths and sequences of nucleosides according to the present invention.

Any suitable solid support materials may be adapted for use in the present invention. Examples of suitable solid support materials include controlled-pore glass ("CPG"), polystyrene, silica, cellulose paper, and combinations of two or more thereof. A preferred class of solid support material includes controlled-pore glass, polystyrene, and combinations thereof.

The solid support for use in the present methods may have pores of any suitable size. As will be recognized by those of skill in the art, the choice of pore size depends at least in part upon the size of the oligomer to be produced and the nucleotide synthesis procedure used. In light of the teachings herein, those of skill in the art will be readily able to select a solid support material of appropriate pore size for use in a wide variety of applications.

A variety of solid-support immobilized nucleosides are available commerically. For example, a number of n-protected deoxynucleosides immobilized on CPG (including 0.2 micromolar Benzoyl-protected deoxycytosine on 1000 angstrom CPG) are available from Applied Biosystems (ABI).

Any of a wide range of Automated DNA/RNA Synthesizers can be adapted for use in the present invention. Examples of suitable DNA Synthesizers include the Model Nos. 3900, 3948, 3400, 380, 380B, 392 and 394, Expedite 8800, 8905, 8909 from Applied Biosystems; Gene Assembler, OligoPilot II, AKTAoligopilot 10, and AKTAoligopilot 100 available from Amersham/GE Healthcare; and Beckmann Oligo 1000 and 1000M, the MWG Biotech Oligo 2000, PolyPlex GeneMachine, Illumina Oligator, MerMade I, II and V, Intelligent BioInstruments Primer Station 960, Proligo Polygen, Syntower, and the like. A preferred class of Synthesizer includes Model ABA-394, and the like.

Additional features of the present invention are provided in the following examples, which should not be construed as limiting the claims.

EXAMPLES

Examples 1-12

The following examples demonstrate the increased solubility of BMT in nitrile upon the addition of the co-solvent an N-methylimidazole (NMI).

| Ex. | Co-solvent | Concentration of BMT (M) | Temp. (° C.) | Time for dissolution (min.) | Shaking | Precipitation (after time/temperature) |
|---|---|---|---|---|---|---|
| 1 | — | 0.25 | 25 | 5 | moderate | */25° C. |
| 2 | — | 0.30 | 25 | 30 | vigorous | */25° C. |
| 3 | — | 0.30 | 35 | 2 | moderate | */25° C. |
| 4 | — | 0.40 | 35 | 10 | vigorous | */25° C. |
| 5 | NMI (0.5%) | 0.35 | 25 | 15 | sonication | No (16 hrs./4° C.) |
| 6 | NMI (0.5%) | 0.40 | 25 | 15 | sonication | No (16 hrs./4° C.) |
| 7 | NMI (0.5%) | 0.35 | 25 | 15 | sonication | No (16 hrs./−1° C.) |
| 8 | NMI (0.5%) | 0.40 | 25 | 15 | sonication | Yes (16 hrs./−1° C.) |
| 9 | NMI (0.5%) | 0.35 | 25 | 15 | sonication | Yes (16 hrs./−4° C.) |
| 10 | NMI (0.5%) | 0.40 | 25 | 15 | sonication | Yes (16 hrs./−4° C.) |
| 11 | NMI (1.0%) | 0.30 | 25 | 5 | gentle | No (24 hrs./−4° C.) |
| 12 | NMI (1.5%) | 0.30 | 25 | 5 | gentle | No (24 hrs./−4° C.) |

*at room temperature, mixtures of BMT in acetonitrile at concentrations higher than 0.25M do not readily form stable solutions As shown in the above-mentioned examples, the concentration of BMT in acetonitrile can be increased via the addition of the co-solvent NMI.

Examples 13-37

The following examples demonstrate the comparative coupling yield and full length product of RNA synthesis utilizing different phosphoramidite activators. The average value for each example was calculated by averaging a total of 3 runs using a rU20 sequence or a RNA 21-mer sequence.

The experimental method for Example 13 was as follows:

A synthesis column containing LCAA-CPG support (15.4 mg) derivatized with r-DMT-U and the Q-linker was installed on an ABI 394 DNA synthesizer. The synthesizer was configured with 0.1 M 2'-O-t-butyldimethylsilyl protected RNA phosphoramidite solutions (Transgenomics) and the deblock, capping, and oxidation solutions normally used. The activator solution used was 0.3 M BMT+2.5% NMI. A standard 0.2 µmol scale RNA synthesis cycle (300 sec coupling time) was performed (Tr-off/manual ending). After synthesis, the crude product was left attached to the support. The synthesis column was opened and a portion of CPG (5.2 mg) was removed and placed in ammonium hydroxide (48 h, RT). The solution was decanted off, NH$_4$OH was removed by evaporation, and the residue was dissolved in water. UV quantitation at 260 nm showed recovery of 27.3 A$_{260}$ units (or 52.5 A$_{260}$ units per 10 mg of CPG)). An aliquot of the 2'-O-silylated crude material (5 A$_{260}$ units) was removed, dissolved in 3:1 DMSO/TEA-3HF (10 µl) and heated (3 h @65°) to deprotect the 2'-OH groups. n-Butanol (1.5 ml) was added to precipitate the completely deprotected product. After centrifugation, the pellet was collected and then analyzed by capillary gel electrophoresis as described above, except that gloves and sterile DEPC water were used to avoid RNase contamination.

This method was repeated for Examples 14-16, except that the 0.45M Tetrazole activator was replaced with the indicated compositions.

Sequence: rGCC CAU AUC GUU UCA UAG CUU (RNA mixed based 21-mer; SEQ ID NO.: 1)

| Ex. | Activator | Phosphoramidite | Coupling Time (s) | Avg. Full Length Product (%) | Avg. Coupling Yield (%) |
|---|---|---|---|---|---|
| 13 | 0.3M BMT + 2.5% NMI | Transgenomic | 300 | 58.20 | 97.3 |
| 14 | 0.3M BMT + 2.5% NMI | Pierce | 120 | 30.64 | 94.3 |
| 15 | 0.3M BMT + 0.5% NMI | Transgenomic | 300 | 68.79 | 98.1 |
| 16 | 0.3M BMT + 0.5% NMI | Transgenomic | 180 | 52.95 | 96.9 |
| 17 | 0.3M BMT + 0.5% NMI | Pierce | 120 | 56.86 | 97.2 |
| 18 | 0.3M BMT + 0.5% NMI | Transgenomic | 120 | 53.07 | 96.9 |
| 19 | 0.3M BMT + 0.5% NMI | Transgenomic | 60 | 44.32 | 96.0 |
| 20 | 0.3M BMT | Pierce | 120 | 47.35 | 96.3 |
| 21 | 0.5M DIEA + TFA | Transgenomic | 300 | 52.45 | 96.8 |
| 22 | 0.5M DIEA + TFA | Transgenomic | 180 | 53.42 | 96.9 |
| 23 | 0.5M DIEA + TFA | Transgenomic | 120 | 54.39 | 97.0 |
| 24 | 0.5M DIEA + TFA | Transgenomic | 60 | 41.02 | 95.6 |
| 25* | 0.45M Tetrazole | Pierce | 600 | 27.84 | 93.8 |
| 26 | 0.45M Tetrazole | Transgenomic | 300 | 47.34 | 96.3 |
| 27 | 0.45M Tetrazole | Transgenomic | 180 | 21.67 | 92.6 |
| 28 | 0.45M Tetrazole | Transgenomic | 120 | 3.30 | 84.3 |
| 29 | 0.45M Tetrazole | Transgenomic | 60 | 0.00 | 0.0 |

*Average of 5 runs.

Sequence: rUUU UUU UUU UUU UUU UUU UU (RNA 20-mer; SEQ ID NO.: 2)

| Ex. | Activator | Phosphoramidite | Coupling Time (s) | Avg. Full Length Product (%) | Avg. Coupling Yield (%) |
|---|---|---|---|---|---|
| 30 | 0.3M BMT + 2.5% NMI | Transgenomic | 300 | 62.04 | 97.5 |
| 31 | 0.3M BMT + 0.5% NMI | Transgenomic | 300 | 67.68 | 98.0 |
| 32 | 0.3M BMT + 0.5% NMI | Pierce | 120 | 66.58 | 98.0 |
| 33*** | 0.3M BMT | Transgenomic | 300 | 66.95 | 97.9 |
| 34** | 0.3M BMT | Pierce | 120 | 63.60 | 97.8 |
| 35*** | 0.25M BMT | Transgenomic | 300 | 68.82 | 98.1 |
| 36 | 0.45M Tetrazole | Transgenomic | 300 | 55.27 | 96.9 |
| 37 | 0.5M DIEA + TFA | Transgenomic | 300 | 59.48 | 97.3 |

**Average of 6 runs.
***Although 0.25M to 0.3M solutions of BMT without NMI may be used successfully in laboratory procedures, these concentrated solutions are not practical for industrial applications because the BMT rapidly precipitates out of solution which can lead to a clogging of transfer lines.

As shown in the above-mentioned examples, the phosphoramidite activator solution of 0.3M BMT can produce a coupling yield and full length RNA oligonucleotide product equal or superior to that of certain other activators. However, high concentrations of NMI could reduce the efficiency of the synthesis processes.

Examples 38-43

The following examples demonstrate the comparative coupling yield and full length product of DNA synthesis utilizing different phosphoramidite activators. The average value for each example was calculated by averaging a total of 3 runs using the indicated DNA sequence.

The experimental method for Example 38 was as follows:

A synthesis column containing LCAA-CPG support (10-15 mg) derivatized with d-DMT-G(iBu) and the Q-linker was installed on an ABI 394 DNA synthesizer. The synthesizer was configured with 0.1 M phosphoramidite solutions (TransGenomics) and the deblock, capping, and oxidation solutions normally used. The activator solution used was 0.3 M BMT+0.5% NMI. A standard 0.2 μmol scale DNA synthesis cycle was performed (Tr-off/auto ending). After synthesis, the crude product was automatically cleaved from the support using ammonium hydroxide (5 min, RT). The material was then heated (55°, 16 h) to remove protecting groups. The NH$_4$OH was removed by evaporation and the residue redissolved in water and quantitated by UV at 260 nm (yield of 59 A$_{260}$ units). An aliquot of the crude material (0.5 A$_{260}$ unit) was removed, redissolved in water (50 μl), and precipitated with n-butanol (1.5 ml) to desalt. The sample was centrifuged (2 min), the liquid layer removed, and the pellet dried under vacuum. The sample was redissolved in 7:3 formamide/water (100 μl), denatured (95°, 2 min), cooled on ice (2 min) and then analyzed by capillary gel electrophoresis. CGE was performed using an Agilent instrument in PEG solution and Agilent PVA coated capillaries (100 μm×33 cm total length) as per Agilent conditions (publication #5988-4303EN). Samples were analyzed in triplicate and the average integrated peak area (corrected for mobility) of the largest peak was used as the overall yield of full-length product.

This method was repeated for Examples 20 and 21, except that the 0.5M ETT activator was replaced with the indicated compositions.

Sequence: dGCC CAA GCT GGC ATC CGT CA (DNA mixed based 20-mer; SEQ ID NO.: 3)

| Ex. | Activator | Phosphoramidite | Coupling Time (s) | Avg. Full Length Product (%) | Avg. Coupling Yield (%) |
|---|---|---|---|---|---|
| 38 | 0.3M BMT + 0.5% NMI | Transgenomic | 60 | 80.59 | 98.9 |
| 39 | 0.5M DIEA + TFA | Transgenomic | 60 | 74.85 | 98.5 |

Sequence: dGGC TAA ATC GCT CCA CCA AG (DNA mixed based 20-mer; SEQ ID NO.: 4)

| Ex. | Activator | Phosphoramidite | Coupling Time (s) | Avg. Full Length Product (%) | Avg. Coupling Yield (%) |
|---|---|---|---|---|---|
| 40 | 0.3M BMT + 0.5% NMI | Transgenomic | 60 | 83.99 | 99.1 |
| 41*** | 0.3M BMT | Transgenomic | 60 | 86.68 | 99.2 |
| 42*** | 0.25M BMT | Transgenomic | 60 | 85.28 | 99.2 |
| 43 | 0.5M DIEA + TFA | Transgenomic | 60 | 79.55 | 98.8 |

***Although 0.25M to 0.3M solutions of BMT without NMI may be used successfully in laboratory procedures, these concentrated solutions are not practical for industrial applications because the BMT rapidly precipitates out of solution which can lead to a clogging of transfer lines.

As shown in the above-mentioned examples, the phosphoramidite activator solution of 0.3M BMT can produce a coupling yield and full length DNA oligonucleotide product comparable to that of other activators.

What is claimed is:

1. A phosphoramidite activator comprising a solution of 5-benzylmercaptotetrazole in acetonitrile and an N-alkylimidazole.

2. The activator of claim 1 comprising at least about 0.5 percent of an N-alkylimidazole by weight.

3. The activator of claim 2 comprising at least about 1.0 percent of an N-alkylimidazole by weight.

4. The activator of claim 3 comprising at least about 1.5 percent of an N-alkylimidazole by weight.

5. The activator of claims 1 wherein the N-alkylimidazole is N-methylimidazole.

6. The activator of claim 1 comprising at least about a 0.25 molar solution of benzylmercaptotetrazole.

7. The activator of claim 1 comprising at least about a 0.30 molar solution of benzylmercaptotetrazole.

8. The activator of claim 1 comprising at least about a 0.35 molar solution of benzylmercaptotetrazole.

9. The activator of claim 1 comprising at least about a 0.40 molar solution of benzylmercaptotetrazole.

10. A method of phosphoramidite activation comprising the steps of:
    (a) providing a phosphoramidite; and
    (b) reacting the phosphoramidite in step (a) with the phosphoramidite activator of claim 1 to produce an intermediate product capable of reacting with a 5'-O site of a nucleoside or oligonucleotide.

11. The method of claim 10, wherein said phosphoramidite has the formula:

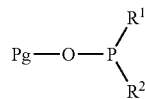

wherein Pg is a phosphorous protecting group selected from the group consisting of —CH$_2$CH$_2$CN, —CH$_2$CH=CHCH$_2$CN, para-CH$_2$C$_6$H$_4$CH$_2$CN, —(CH$_2$)$_{2-5}$N(H)COCF$_3$, —CH$_2$CH$_2$Si(C$_6$H$_5$)$_2$CH$_3$, and CH$_2$CH$_2$N(CH$_3$)COCF$_3$;

R$^1$ is a nucleoside or an oligonucleotide; and

R$^2$ is morpholino, dialkylamino, or —N(R$^3$)$_2$, wherein R$^3$ is independently C$_1$-C$_6$ alkyl or 4-7 member heterocycloalkyl or heterocycloalkyenyl ring having up to 3 heteroatoms selected from the group consisting of nitrogen, sulfur, and oxygen.

12. A method of preparing an oligonucleotide comprising the steps of:
    (a) providing a 3'-nucleoside phosphoramidite or 3'-oligonucleotide phosphoramidite; and
    (b) reacting said 3'-nucleoside phosphoramidite or 3'-oligonucleotide phosphoramidite with the 5'-hydroxyl of a nucleoside, or oligonucleotide in the presence of a phosphoramidite activator;
    wherein said phosphoramidite activator comprises a solution of 5-benzylmercaptotetrazole in acetonitrile and N-alkylimidazole, said solution having a 5-benzylmercaptotetrazole concentration greater than about 0.25M.

13. The method of claim 12 wherein said nucleoside or oligonucleotide is bound to a solid support.

14. A method for preparing covalent intersugar linkages in an oligonucleotide synthesis comprising the steps of:
    (a) providing a phosphoramidite; and
    (b) reacting said phosphoramidite with a hydroxyl group of the sugar moiety of a nucleoside or an oligonucleotide in the presence of a phosphoramidite activator to produce a compound having the formula:

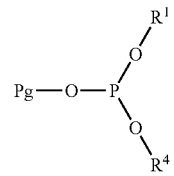

wherein Pg is a phosphorous protecting group selected from the group consisting of —CH$_2$CH$_2$CN, —CH$_2$CH=CHCH$_2$CN, para-CH$_2$C$_6$H$_4$CH$_2$CN, —(CH$_2$)$_{2-5}$N(H)COCF$_3$, —H$_2$CH$_2$Si(C$_6$H$_5$)$_2$CH$_3$, and CH$_2$CH$_2$N(CH$_3$)COCF$_3$;

R$^1$ is a nucleoside or an oligonucleotide; and

R$^4$ is a nucleoside or a oligonucleotide;

said phosphoramidite activator comprising a solution of at least 0.25M 5-benzylmercaptotetrazole in acetonitrile and N-alkylimidazole.

15. The method of claim 14 wherein said phosphoramidite has the formula:

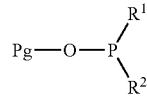

wherein Pg is a phosphorous protecting group selected from the group consisting of —CH$_2$CH$_2$CN, —CH$_2$CH=CHCH$_2$CN, para-CH$_2$C$_6$H$_4$CH$_2$CN, —(CH$_2$)$_{2-5}$N(H)COCF$_3$, —CH$_2$CH$_2$Si(C$_6$H$_5$)$_2$CH$_3$, and CH$_2$CH$_2$N(CH$_3$)COCF$_3$;

R$^1$ is a nucleoside or an oligonucleotide; and

R$^2$ is morpholino, dialkylamino, or —N(R$^3$)$_2$, wherein R$^3$ is independently C$_1$-C$_6$ alkyl or 4-7 member heterocycloalkyl or heterocycloalkyenyl ring having up to 3 heteroatoms selected from the group consisting of nitrogen, sulfur, and oxygen.

16. The method of claim 14, further comprising wherein the steps (a) and (b) are performed iteratively in appropriate sequence with standard process steps including deprotection, oxidation of phosphorus (III) to phosphorus (V), and capping to produce an oligonucleotide according to a preselected nucleotide base sequence.

\* \* \* \* \*

UNITED STATES PATENT AND TRADEMARK OFFICE
CERTIFICATE OF CORRECTION

PATENT NO. : 7,339,052 B2  
APPLICATION NO. : 11/053733  
DATED : March 4, 2008  
INVENTOR(S) : Kalakota S. Reddy Page 1 of 1

It is certified that error appears in the above-identified patent and that said Letters Patent is hereby corrected as shown below:

Column 6, line 40, to column 7, line 1, the reaction mechanism scheme should appear as follows:

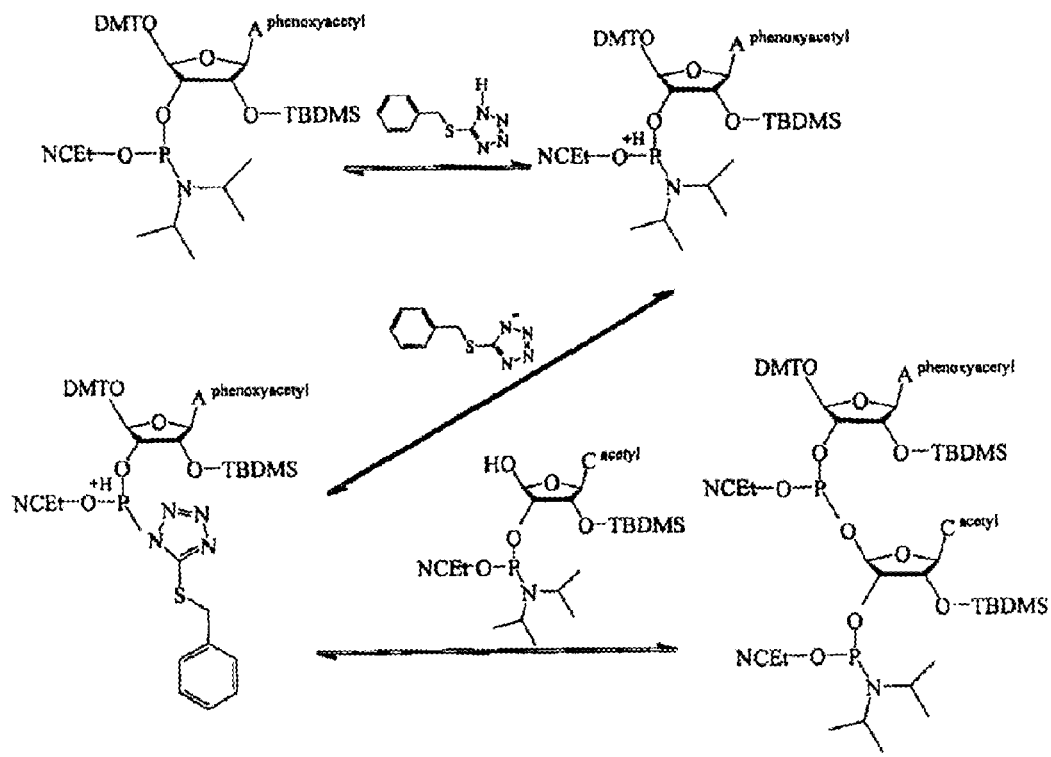

Signed and Sealed this

Twenty-fourth Day of February, 2009

JOHN DOLL  
*Acting Director of the United States Patent and Trademark Office*